US009511283B2

(12) United States Patent
Saukkonen (10) Patent No.: US 9,511,283 B2
(45) Date of Patent: Dec. 6, 2016

(54) METHOD AND APPARATUS FOR COMPARING CURRENT ACTIVITY DATA TO CAPTURED REFERENCE ACTIVITY DATA

(71) Applicant: Timo Saukkonen, Oulu (FI)

(72) Inventor: Timo Saukkonen, Oulu (FI)

( * ) Notice: Subject to any disclaimer, the term of this patent is extended or adjusted under 35 U.S.C. 154(b) by 222 days.

(21) Appl. No.: 14/365,220

(22) PCT Filed: Dec. 11, 2012

(86) PCT No.: PCT/FI2012/051223
§ 371 (c)(1),
(2) Date: Jun. 13, 2014

(87) PCT Pub. No.: WO2013/087987
PCT Pub. Date: Jun. 20, 2013

(65) Prior Publication Data
US 2014/0337369 A1 Nov. 13, 2014

(30) Foreign Application Priority Data
Dec. 16, 2012 (FI) ..................................... 20116280

(51) Int. Cl.
*G06F 17/30* (2006.01)
*A63F 13/217* (2014.01)
(Continued)

(52) U.S. Cl.
CPC .............. *A63F 13/217* (2014.09); *A63F 13/28* (2014.09); *G06F 17/30386* (2013.01);
(Continued)

(58) Field of Classification Search
None
See application file for complete search history.

(56) References Cited

U.S. PATENT DOCUMENTS 3,875,388 A * 4/1975 Luten ...................... B63H 9/00
701/21
6,308,649 B1 * 10/2001 Gedeon ................... B63B 49/00
114/39.11
(Continued)

FOREIGN PATENT DOCUMENTS

GB          2365790 A      2/2002

OTHER PUBLICATIONS

Extended European Search Report, Application No. 12858016.4-1972/2790797 PCT/FI2012051223; Dated Jun. 23, 2015; 7 Pages.
(Continued)

*Primary Examiner* — Anh Tai Tran
(74) *Attorney, Agent, or Firm* — Ziegler IP Law Group, LLC (57) ABSTRACT

An apparatus includes a communication interface for receiving reference activity data items, current activity data, and current environmental data; at least one processor; and at least one memory including computer program code; wherein the at least one memory and the computer program code configured to, with the at least one processor, cause the apparatus to maintain a reference activity data item relating to a previous activity, which reference activity data item includes reference activity data associated with reference environmental data; receive current activity data and current environmental data relating to a current activity; determine the reference activity data associated with the reference environmental data corresponding to the current environmental data; compare the current activity data with the reference activity data; and provide feedback for a user of the apparatus in response to the comparison.

12 Claims, 4 Drawing Sheets (51) Int. Cl.
*A63F 13/28* (2014.01)
*G06F 19/00* (2011.01)
*G01C 21/20* (2006.01)

(52) U.S. Cl.
CPC ... *A63F 2300/205* (2013.01); *A63F 2300/513* (2013.01); *A63F 2300/5573* (2013.01); *A63F 2300/69* (2013.01); *G01C 21/203* (2013.01); *G06F 19/3481* (2013.01)

(56) References Cited

U.S. PATENT DOCUMENTS

| | | | |
|---|---|---|---|
| 6,611,737 B1* | 8/2003 | El-Tahan | G05D 1/0206 701/21 |
| 6,868,338 B1 | 3/2005 | Elliott | |
| 2006/0247070 A1 | 11/2006 | Funk et al. | |
| 2007/0282560 A1 | 12/2007 | Anderson | |
| 2010/0230370 A1* | 9/2010 | Schneider | B63B 27/10 212/276 |
| 2011/0039624 A1 | 2/2011 | Potkonjak | |
| 2011/0124469 A1 | 5/2011 | Uhlir et al. | |

OTHER PUBLICATIONS

Written Opinion of the International Preliminary Examining Authority; PCT/FI2012/051223; Feb. 25, 2014.
International Search Report and the Written Opinion of the International Searching Authority; PCT/FI2012/051223; Apr. 12, 2013.

* cited by examiner

METHOD AND APPARATUS FOR COMPARING CURRENT ACTIVITY DATA TO CAPTURED REFERENCE ACTIVITY DATA

TECHNICAL FIELD

The present application generally relates to a method and an apparatus for comparing a recorded activity to an ongoing activity. The present application further relates to a method and an apparatus for providing feedback to a user based on the comparison.

BACKGROUND ART

Many people who exercise strive to improve their performance. A bicyclist or a sailor, for example, may desire to improve performance by increasing speed over a defined known distance and/or route.

One well-known method exercisers may use to improve performance is to set and strive to reach performance goals. This requires that the exerciser measure performance during the training session and compare the measured performance to the pre-defined goals. For example, if an exerciser desires to increase his or her average running speed, he or she would set an average speed goal, measure an actual average speed during a training session, and then compare the average speed goal with the actual average speed. In this manner, the exerciser is provided with performance feedback that can be used as a guide for future training sessions. To measure actual average speed, an exerciser typically measures an elapsed time of the training session using a stopwatch, measures the distance traveled during the session using a map or landmarks, and divides the distance traveled by the elapsed time. Unfortunately, this requires that the exerciser carry the stopwatch and remember to start and stop the stopwatch at appropriate points during the training session. It also requires that the exerciser determine the distance traveled.

If the exerciser uses a non-standard or arbitrarily-defined course, the distance can sometimes be roughly determined from a vehicle's odometer, though the result may be significantly inaccurate. Where the course cannot be driven with a vehicle, such as, for example, where the course is over open country or over water, some other means of determining distance must be devised. Pedometers, for example, are known in the prior art for measuring distance traveled. Unfortunately, pedometers suffer from a number of disadvantages, including, for example, that they must be properly calibrated; are inaccurate for most forms of movement other than running; and the runner must maintain consistent strides regardless of such factors as changing terrain. Following an arbitrary course can also make repeating the course extremely difficult because the exerciser may not recall the course's exact route. Furthermore, this method makes it very difficult for the user to be aware of performance and progress toward reaching the pre-defined goals during the training session.

Further problems arise, when the exerciser trains in an environment that is affected by environmental parameters such as wind or topography. Topography may comprise for example inclination of a ground surface or flute height. A solution is needed for providing training feedback for the exerciser in such environment.

SUMMARY

According to a first example aspect of the invention there is provided an apparatus comprising:
  a communication interface for receiving reference activity data items, current activity data, and current environmental data;
  at least one processor; and
  at least one memory including computer program code;
    wherein the at least one memory and the computer program code configured to, with the at least one processor, cause the apparatus to:
  maintain a reference activity data item relating to a previous activity, which reference activity data item comprising reference activity data associated with reference environmental data;
  receive current activity data and current environmental data relating to a current activity;
  determine the reference activity data associated with the reference environmental data corresponding to the current environmental data;
  compare the current activity data with the reference activity data; and
  provide feedback for a user of the apparatus in response to the comparison.

In an embodiment, the at least one memory and the computer program code are further configured to, with the at least one processor, cause the apparatus to:
  maintain the reference activity data items relating to previous activities, which reference activity data items comprise reference activity data associated with reference environmental data; and
  receive the current activity data and the current environmental data relating to a current activity.

The environmental data may comprise at least one of the following:
  topography information; and
  wind information.

The topography information may comprise at least one of the following:
  flute height information; and
  ground slope information.

In an embodiment, the apparatus further comprises at least one of the following devices for providing the current environmental data:
  an anemometer for providing wind information;
  a sensor for providing flute height information; and
  a satellite based positioning device for providing location information.

In an embodiment, the location information may comprise at least one of the following:
  position coordinates;
  speed;
  direction of movement; and
  slope information.

According to a second example aspect of the invention there is provided a method comprising:
  maintaining a reference activity data item relating to a previous activity, which reference activity data item comprising reference activity data associated with reference environmental data;
  receiving current activity data and current environmental data relating to a current activity;
  determining the reference activity data associated with the reference environmental data corresponding to the current environmental data;

comparing the current activity data with the reference activity data; and providing feedback for a user of an apparatus in response to the comparison.

In an embodiment, the method further comprises:

maintaining the reference activity data items relating to previous activities, which reference activity data items comprise reference activity data associated with reference environmental data; and receiving the current activity data and the current environmental data relating to a current activity.

In an embodiment, the method further comprises receiving at least one of the following:

wind information;

flute height information; and location information.

In an embodiment, the reference activity data and the current activity data comprise at least one of the following:

sailing data; and cycling data.

According to a third example aspect of the invention there is provided a computer program embodied on a computer readable medium comprising computer executable program code which, when executed by at least one processor of an apparatus, causes the apparatus to:

maintain a reference activity data item relating to a previous activity, which reference activity data item comprising reference activity data associated with reference environmental data;

receive current activity data and current environmental data relating to a current activity;

determine the reference activity data associated with the reference environmental data corresponding to the current environmental data;

compare the current activity data with the reference activity data; and provide feedback for a user of the apparatus in response to the comparison.

Different non-binding example aspects and embodiments of the present invention have been illustrated in the foregoing. The above embodiments are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

The invention will be described, by way of example only, with reference to the accompanying drawings, in which.

DETAILED DESCRIPTION

In the following description, like numbers denote like elements.

Figure 1:
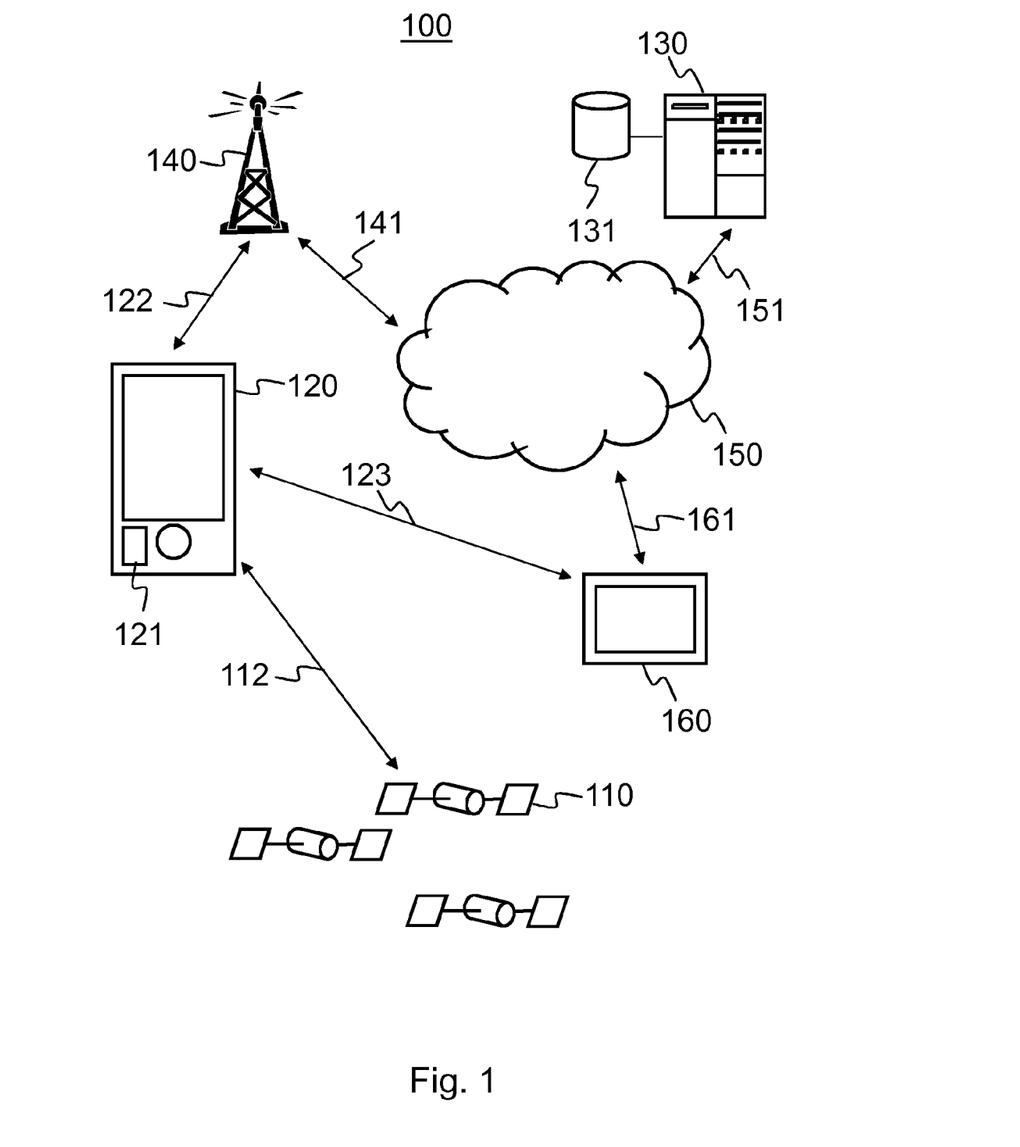
FIG. 1 shows a schematic picture of a system according to an example embodiment of the invention.

FIG. 1 shows a schematic picture of a system 100 according to an example embodiment of the invention. The system 100 comprises a plurality of satellites 110 in orbit about the Earth. The orbit of each satellite 110 is not necessarily synchronous with the orbits of other satellites and, in fact, is likely asynchronous. A global positioning system receiver apparatus such as the ones described in connection with preferred embodiments of the present invention is shown receiving spread spectrum global positioning system (GPS) satellite signals 112 from the various satellites 110.

A user apparatus 120 may comprise a mobile phone, an internet tablet, a mobile terminal or a laptop computer, for example. The user apparatus 120 is capable of downloading and locally executing software program code. The software program code may be a client application of a service whose server application is running on the server apparatus 130 of the system 100. The user apparatus 120 may comprise an environmental and current activity data capturing element 121, such as a wind sensor, a barometer, a GPS receiver and a flute height sensor, for example. The user apparatus 120 is configured to be connectable to a wireless communication network 140 over a wireless connection 122. The wireless connection 122 may comprise a mobile cellular network or a wireless local area network (WLAN), for example. The wireless communication network may be to a public data communication network 150, for example the Internet, over a data connection 141.

In an embodiment, the system 100 comprises a computer apparatus 160 configured to be connectable to the user apparatus 120 over a data connection 123. The data connection 123 may comprise a wired connection or a wireless connection. The wired connection may comprise Universal Serial Bus (USB), High-Definition Multimedia Interface (HDMI) or local area network (LAN), for example. The wireless connection may comprise Bluetooth™, Radio Frequency Identification (RF-ID) or wireless local area network (WLAN), for example. The computer apparatus 160 may be connected to a public data communication network 150, for example the Internet, over a data connection 161.

In an embodiment, the system 100 comprises a server apparatus 130, which comprises a storage device 131 for storing reference activity data items comprising reference activity data associated with reference environmental data, over data connection 151.

In an embodiment, reference activity data items may travel to a user apparatus 120 over different paths. A first path may comprise sending reference activity data captured earlier by another user over a wireless communication network 122, 140, 141 and public data communication network 150, 151 from the server apparatus 130. A second path may comprise sending earlier captured reference activity data to the computer apparatus 160 and therefrom over the data connection 123 to the user apparatus 120.

In an embodiment, a proprietary application in the user apparatus 120 may be a client application of a service whose server application is running on the server apparatus 130 of the system 100. The proprietary application may capture the reference activity data to be stored at the server 130, 131. Also reference environmental data for the captured reference activity data may be retrieved by the proprietary application from the capturing elements 121 of the user apparatus 120.

In an embodiment, the proprietary application may capture current activity data to be processed at the user apparatus 120. Also current environmental data for the captured activity may be retrieved by the proprietary application from the capturing elements 121 of the user apparatus 120.

Figure 2:
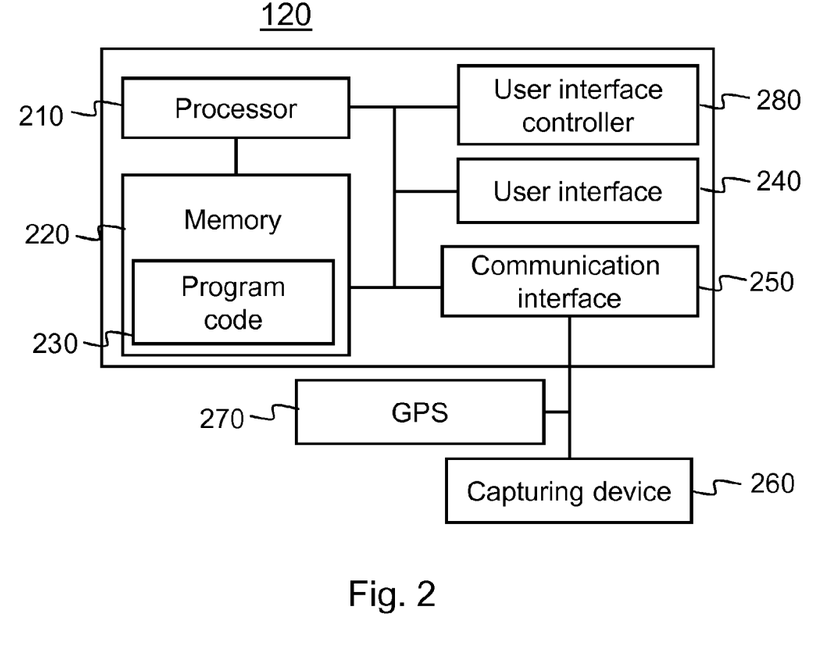
FIG. 2 presents an example block diagram of a user apparatus in which various embodiments of the invention may be applied.

FIG. 2 presents an example block diagram of a user apparatus 120 in which various embodiments of the invention may be applied. The user apparatus 120 may be a user equipment (UE), user device or apparatus, such as a mobile terminal, a smart phone or other communication device.

The general structure of the user apparatus 120 comprises a user interface 240, a communication interface 250, a satellite positioning device (GPS) 270, a capturing device 260 for capturing current activity data and current environmental data, a processor 210, and a memory 220 coupled to the processor 210. The user apparatus 120 further comprises software 230 stored in the memory 220 and operable to be loaded into and executed in the processor 210. The software 230 may comprise one or more software modules and can be in the form of a computer program product. The user apparatus 210 may further comprise a user interface controller 280.

The processor 210 may be, e.g., a central processing unit (CPU), a microprocessor, a digital signal processor (DSP), a graphics processing unit, or the like. FIG. 2 shows one processor 210, but the user apparatus 120 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The user apparatus 120 may comprise a plurality of memories. The memory 220 may be constructed as a part of the user apparatus 120 or it may be inserted into a slot, port, or the like of the user apparatus 120 by a user. The memory 220 may serve the sole purpose of storing data, or it may be constructed as a part of an apparatus serving other purposes, such as processing data. A proprietary activity application, activity data and environmental data may be stored to the memory 220.

The user interface controller 280 may comprise circuitry for receiving input from a user of the user apparatus 120, e.g., via a keyboard, graphical user interface shown on the display of the user interfaces 240 of the user apparatus 120, speech recognition circuitry, or an accessory device, such as a headset, and for providing output to the user via, e.g., a graphical user interface or a loudspeaker.

The satellite positioning device 270 is configured to provide location information. Such information may comprise, for example, position coordinates, speed, direction of movement; and slope information.

The communication interface module 250 implements at least part of data transmission. The communication interface module 250 may comprise, e.g., a wireless or a wired interface module. The wireless interface may comprise such as a WLAN, Bluetooth, infrared (IR), radio frequency identification (RF ID), GSM/GPRS, CDMA, WCDMA, or LTE (Long Term Evolution) radio module. The wired interface may comprise such as universal serial bus (USB) or National Marine Electronics Association (NMEA) 0183/2000 standard for example. The communication interface module 250 may be integrated into the user apparatus 120, or into an adapter, card or the like that may be inserted into a suitable slot or port of the user apparatus 120. The communication interface module 250 may support one radio interface technology or a plurality of technologies. The user apparatus 120 may comprise a plurality of communication interface modules 250.

A skilled person appreciates that in addition to the elements shown in FIG. 2, the user apparatus 120 may comprise other elements, such as microphones, extra displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the user apparatus 120 may comprise a disposable or rechargeable battery (not shown) for powering when external power if external power supply is not available.

In an embodiment, the user apparatus 120 comprises speech recognition means. Using these means, a pre-defined phrase may be recognized from the speech and translated into control information for the apparatus 120, for example.

The satellite positioning device 270 and the capturing device 260 may be configured to be comprised by the user apparatus 120 or connected as separate devices to the apparatus 120. In case the satellite positioning device 270 and the capturing device 260 are comprised in the apparatus 120 they may be connected to the apparatus 120 using an internal bus of the apparatus 120. In case the satellite positioning device 270 and the capturing device 260 are external devices connected to the apparatus 120 they may be connected to the apparatus 120 using communication interface 250 of the apparatus 120 or using the internal bus.

Figure 3:
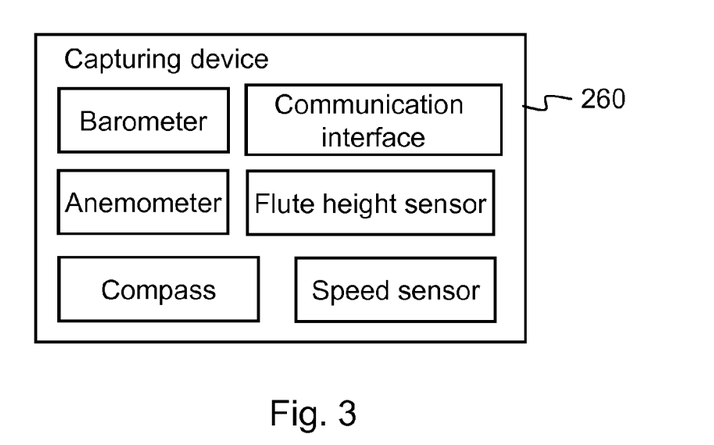
FIG. 3 presents an example block diagram of a capturing device in which various embodiments of the invention may be applied.

FIG. 3 presents an example block diagram of a capturing device 260 in which various embodiments of the invention may be applied. The capturing device 260 may comprise various means for activity data detection and environmental data detection, for example. The capturing device 260 may be used for both reference data and current data capturing.

In an embodiment, the capturing device 260 may comprise at least one of the following devices:
   an anemometer for providing wind information;
   a wind sensor for providing wind information;
   a sensor for providing flute height information;
   a barometer for measuring air pressure;
   a temperature sensor for measuring environmental temperature;
   a water depth sensor for measuring depth information;
   a chart plotter for providing position information;
   a sail sensor for providing sail information;
   a speed sensor for providing speed information;
   a video camera for providing a video signal; and
   a compass for providing direction information.

The capturing device 260 may also comprise several capturing devices 260, combinations of any above mentioned devices, and the like. The environmental temperature may comprise air temperature, water temperature or ground surface temperature, for example.

In an embodiment, a wind sensor 260 is configured to determine or measure wind angle and wind speed. The wind sensor 260 may comprise any element of combination of elements operable to sense wind-related information for use by the user apparatus 120. For example, the wind sensor 260 may be operable to sense apparent wind speed, apparent wind angle, true wind speed, true wind angle, wind velocity made good (VMG), combinations thereof, and the like.

In an embodiment, a sail sensor 260 is configured to determine sail information. The sail information provides status of the currently used sails in a boat and timing of their changes. The sail sensor 260 may comprise a first sensor in a mast of the boat and a second sensor in the sail to identify which sail is used in the mast. Based on the information received from these sensors the user apparatus 120 may define which sails are used in which masts and the times of changing the sails. The sail information may be thus used as a part of the reference activity data and current activity data.

In an embodiment, a video camera 260 is configured to provide video signal. Based on the video signal the user apparatus 120 may determine at least part of the environmental data. For example flute height may be determined based on the video signal from the video camera 260. The determination may be done by video image processing, pattern recognition, measuring a rocking movement or relative movement of a horizon, for example.

The capturing device 260 may comprise communication interface module implementing at least part of data transmission. The communication interface module may comprise, e.g., a wireless or a wired interface module. The wireless interface may comprise such as a WLAN, Bluetooth, infrared (IR), radio frequency identification (RF ID), GSM/GPRS, CDMA, WCDMA, or LTE (Long Term Evolution) radio module. The wired interface may comprise such as universal serial bus (USB) or National Marine Electronics Association (NMEA) 0183/2000 standard for example. The communication interface module may be integrated into the capturing device 260, or into an adapter, card or the like that may be inserted into a suitable slot or port of the capturing device 260. The communication interface module may support one radio interface technology or a plurality of technologies. The capturing device 260 may comprise a plurality of communication interface modules.

Figure 4:
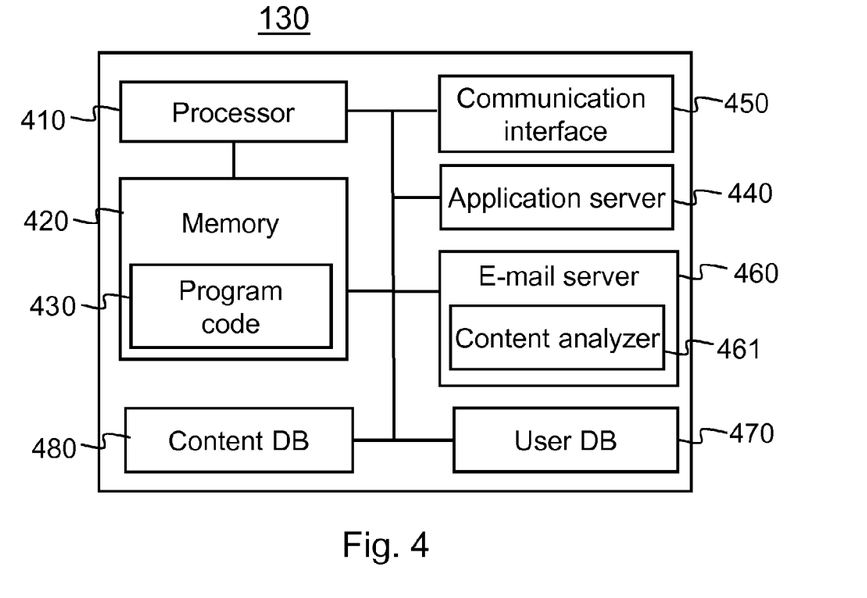
FIG. 4 presents an example block diagram of a server apparatus in which various embodiments of the invention may be applied.

FIG. 4 presents an example block diagram of a server apparatus 130 in which various embodiments of the invention may be applied.

The general structure of the server apparatus 130 comprises a processor 410, and a memory 420 coupled to the processor 410. The server apparatus 130 further comprises software 430 stored in the memory 420 and operable to be loaded into and executed in the processor 410. The software 430 may comprise one or more software modules and can be in the form of a computer program product.

The processor 410 may be, e.g., a central processing unit (CPU), a microprocessor, a digital signal processor (DSP), a graphics processing unit, or the like. FIG. 4 shows one processor 410, but the server apparatus 130 may comprise a plurality of processors.

The memory 420 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 420 may be constructed as a part of the server apparatus 130 or it may be inserted into a slot, port, or the like of the server apparatus 130 by a user. The memory 420 may serve the sole purpose of storing data, or it may be constructed as a part of an apparatus serving other purposes, such as processing data.

The communication interface module 450 implements at least part of radio transmission. The communication interface module 450 may comprise, e.g., a wireless or a wired interface module. The wireless interface may comprise such as a WLAN, Bluetooth, infrared (IR), radio frequency identification (RF ID), GSM/GPRS, CDMA, WCDMA, or LTE (Long Term Evolution) radio module. The wired interface may comprise such as universal serial bus (USB) or National Marine Electronics Association (NMEA) 0183/2000 standard for example. The communication interface module 450 may be integrated into the server apparatus 130, or into an adapter, card or the like that may be inserted into a suitable slot or port of the server apparatus 130. The communication interface module 450 may support one radio interface technology or a plurality of technologies. Captured activity data associated with environmental data of the user apparatus 120 may be received by the server apparatus 130 using the communication interface 450.

The e-mail server process 460, which receives e-mail messages sent from user apparatuses 120 and computer apparatuses 160 via the network 150. The server 460 may comprise a content analyzer module 461, which checks if the content of the received message meets the criteria that are set for new activity data item of the service. The content analyzer module 461 may for example check whether the e-mail message contains a valid activity data item to be used as reference data item. The valid reference data item received by the e-mail server is then sent to an application server 440, which provides application services e.g. relating to the user accounts stored in a user database 470 and content of the content management service. Content provided by the service system 100 is stored in a content database 480.

A skilled person appreciates that in addition to the elements shown in FIG. 4, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like.

Figure 5:
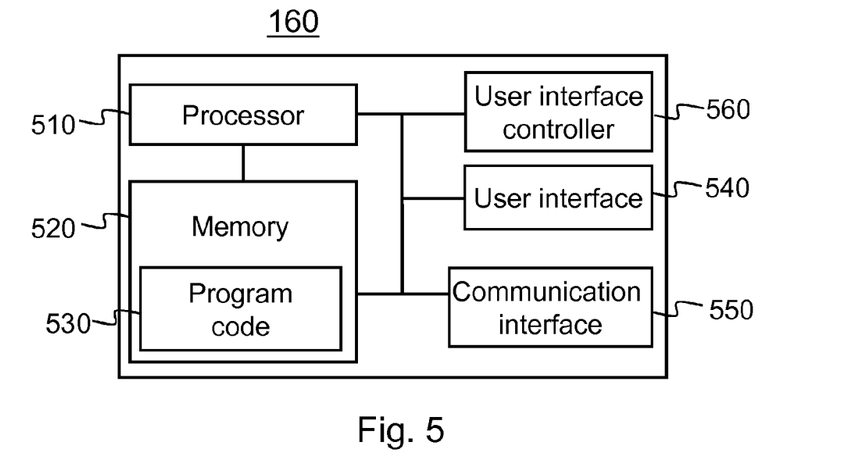
FIG. 5 presents an example block diagram of a computer apparatus in which various embodiments of the invention may be applied.

FIG. 5 presents an example block diagram of a computer apparatus 160 in which various embodiments of the invention may be applied. The computer apparatus 160 may be a user equipment (UE), user device or apparatus, such as a mobile terminal, a smart phone, a laptop computer, a desktop computer or other communication device.

The general structure of the computer apparatus 160 comprises a user interface 540, a communication interface 550, a processor 510, and a memory 520 coupled to the processor 510. The computer apparatus 160 further comprises software 530 stored in the memory 520 and operable to be loaded into and executed in the processor 510. The software 530 may comprise one or more software modules and can be in the form of a computer program product. The computer apparatus 160 may further comprise a user interface controller 560.

The processor 510 may be, e.g., a central processing unit (CPU), a microprocessor, a digital signal processor (DSP), a graphics processing unit, or the like. FIG. 5 shows one processor 510, but the computer apparatus 160 may comprise a plurality of processors.

The memory 520 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The computer apparatus 160 may comprise a plurality of memories. The memory 520 may be constructed as a part of the computer apparatus 160 or it may be inserted into a slot, port, or the like of the computer apparatus 160 by a user. The memory 520 may serve the sole purpose of storing data, or it may be constructed as a part of an apparatus serving other purposes, such as processing data.

The user interface controller 560 may comprise circuitry for receiving input from a user of the computer apparatus 160, e.g., via a keyboard, graphical user interface shown on the display of the user interfaces 240 of the computer apparatus 160, speech recognition circuitry, or an accessory device, such as a headset, and for providing output to the user via, e.g., a graphical user interface or a loudspeaker.

The communication interface module 550 implements at least part of radio transmission. The communication interface module 550 may comprise, e.g., a wireless or a wired interface module. The wireless interface may comprise such as a WLAN, Bluetooth, infrared (IR), radio frequency identification (RF ID), GSM/GPRS, CDMA, WCDMA, or LTE (Long Term Evolution) radio module. The wired interface may comprise such as universal serial bus (USB) or National Marine Electronics Association (NMEA) 0183/2000 standard for example. The communication interface module 550 may be integrated into the computer apparatus 160, or into an adapter, card or the like that may be inserted into a suitable slot or port of the computer apparatus 160. The communication interface module 550 may support one radio interface technology or a plurality of technologies. The computer apparatus 160 may comprise a plurality of communication interface modules 550. Reference activity data items may be downloaded from the server apparatus 130 and stored to the computer apparatus 160. Stored reference activity data items may then be transferred from the computer apparatus 160 to the user apparatus 120 before starting a training session, for example.

A skilled person appreciates that in addition to the elements shown in FIG. 5, the computer apparatus 160 may comprise other elements, such as microphones, extra displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the computer apparatus 160 may comprise a disposable or rechargeable battery (not shown) for powering when external power if external power supply is not available.

Figure 6:
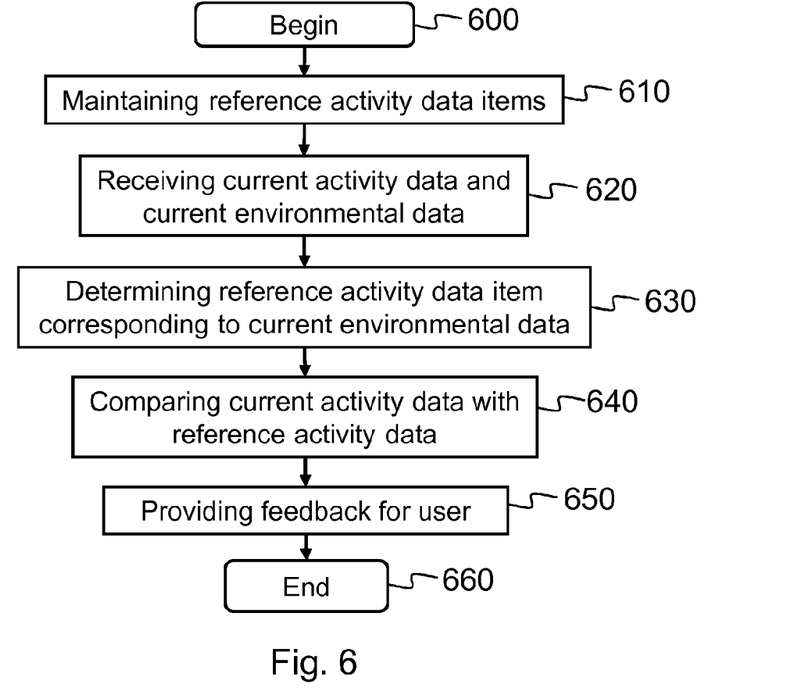
FIG. 6 shows a flow diagram showing operations in accordance with an example embodiment of the invention.

FIG. 6 shows a flow diagram showing operations in accordance with an example embodiment of the invention. In step 600, the method is started. In step 610, reference activity data items are maintained. Current activity data and current environmental data are received in step 620. In step 630, a reference activity data item associated with reference environmental data, corresponding to the current environmental data, is selected. The current activity data is compared with reference activity data of the determined reference activity data item in step 640. In step 650, feedback is provided for a user of the apparatus in response to the comparison. The method is ended in step 660.

Figure 7:
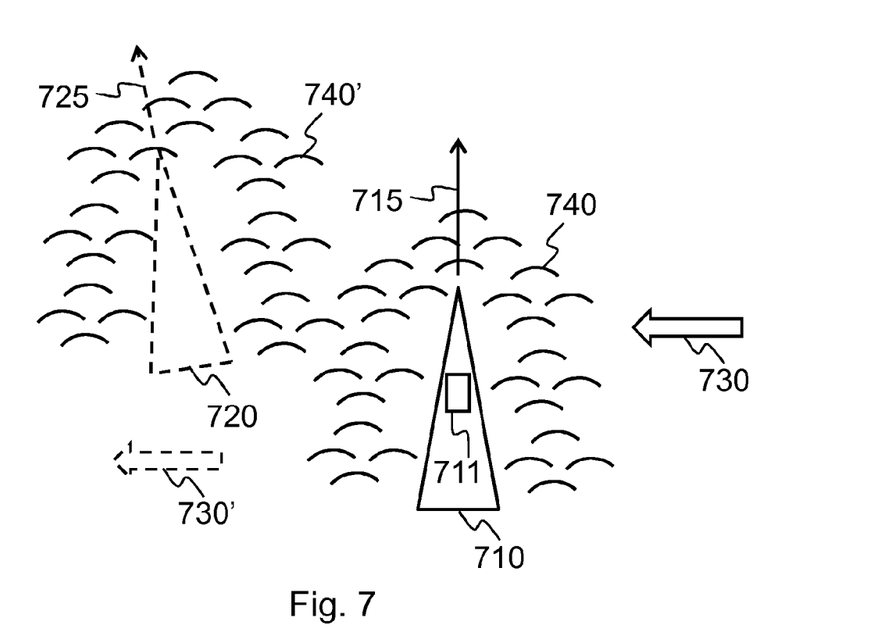
FIG. 7 shows a schematic picture of a system according to an example embodiment of the invention.

FIG. 7 shows a schematic picture of a system according to an example embodiment of the invention. Current activity that is being illustrated relates to sailing. A sailing boat 710 may comprise a user apparatus 711 as described earlier in this application. The user apparatus 711 may further comprise at least one capturing device and a satellite positioning device, for example. The capturing device and the satellite positioning device may provide current activity data and current environmental data for the sailing boat 710. The user apparatus 711 is configured to receive the current activity data, such as location information and a velocity vector 715 of the sailing boat 710, for example. The location information may comprise location coordinates provided by a GPS device and the velocity vector 715 may comprise a speed and a direction of the sailing boat 710, for example. The user apparatus 711 is further configured to receive current environmental data, such as a wind vector 730 and flute height information 740.

FIG. 7 further shows a virtual reference sailing boat 720. The virtual reference sailing boat 720 illustrates a reference sailing performance taken place earlier and captured using a user apparatus similar to the user apparatus 711. Reference data items comprise earlier captured sailing performances in certain environmental conditions. The environmental conditions may comprise for example a wind vector 730' and flute height information 740'. The reference activity data items comprising reference activity data and reference environmental data are stored to the user apparatus 711 for training situation. In training, a reference data item from the stored reference data items may be selected that corresponds to the current environmental data of a wind vector 730 and flute height information 740. The selected reference data item thus comprises the reference activity data and the reference environmental data. The reference activity data and the reference environmental data may have been provided by the capturing device and the satellite positioning device of the sailing boat capturing the performance and illustrated as the virtual sailing boat 720. The reference data item may comprise reference activity data, such as location information and a velocity vector 725 of the sailing boat 720, for example. The location information may comprise location coordinates provided by a GPS device and the velocity vector 725 may comprise a speed and a direction of the sailing boat 720, for example. The reference data item is further configured to comprise reference environmental data, such as a wind vector 730' and flute height information 740'.

In an embodiment, the user apparatus 711 compares the current activity data of the sailing boat 710 to the reference activity data of the virtual sailing boat 720. Such comparison may include location information, heading direction (e.g. degrees) or speed vector of the sailing boat, for example. In response to the comparison, the user apparatus 711 is configured to provide feedback to a user of the apparatus 711 of the sailing boat 710. The feedback may comprise distance information between the boats 710, 720, speed difference between the boats 710, 720, time difference between the boats 710, 720 or direction difference between the boats 710, 720, for example.

In an embodiment, a route with waypoints is stored as reference activity data to a service server. Same route with similar waypoints may be trained by a user with a user apparatus. The user may select from a service server 130 a set of reference activity data items for a certain route. The selected reference data items may comprise reference data associated with preferred reference environmental data. The user may use for example weather forecasts to download such reference activity data items to the user apparatus 711 that correspond to the forecasted wind and flute height for the train route. Such data items may be stored to the user apparatus 711 before training. In training session, the user apparatus 711 may use the closest available reference activity data item in view of the environmental data for comparing to the current activity data. Thus the user may receive valuable real-time feedback of the sailing boat 710 performance compared to the reference performance of the sailing boat 720 captured by a world champion, for example.

In an embodiment, the feedback may be given as audio information, video information, still image information, graphical information, textual information or tactile feedback, for example.

In an embodiment, the user apparatus 711 may use at least two reference activity data items for comparing to the current activity data. The at least two reference activity data items may be processed and a virtual reference activity data item may be created based on processing. Such approach can be used for example when there is no close hit for a reference activity data item based on current environmental data. The virtual reference activity data item may be a mean value of two closest reference data items based on the environmental data.

In an embodiment, the wind vector 730, 730' may represent real wind vector or relative wind vector for a moving sail boat 710, 720. The velocity vector 715, 725 may represent real velocity vector or relative velocity vector in view of a next waypoint of a route.

In an embodiment, at least one sensor for the user apparatus 711 may be located in an escort boat following the moving sailing boat 710, 720. For example wind sensor, flute height sensor and speed sensor might be placed in the escort boat to gather the needed environmental data to be used by the user apparatus 711. The gathered environmental data may be transmitted to the moving sailing boat 710, 720 over a wireless link, for example.

As a sailboat cannot move directly into the wind, it must sail in a zigzag pattern, forming a shallow angle with the wind. In order to achieve the maximum possible speed in such a maneuver, it is important that the boat maintains a certain wind angle. Each boat has an ideal wind angle, which varies depending on the design of the sails and the shape of the hull.

Various embodiments have been presented. It should be appreciated that in this document, words comprise, include and contain are each used as open-ended expressions with no intended exclusivity. If desired, the different functions discussed herein may be performed in a different order and/or concurrently with each other. Furthermore, if desired, one or more of the above-described functions may be optional or may be combined. Although various aspects of the invention are set out in the independent claims, other aspects of the invention comprise other combinations of features from the described embodiments and/or the dependent claims with the features of the independent claims, and not solely the combinations explicitly set out in the claims.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means or in different combinations of embodiments without deviating from the characteristics of the invention.

Furthermore, some of the features of the above-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

The invention claimed is:

1. An apparatus comprising:
   a communication interface for receiving reference activity data items, current activity data, and current environmental data;
   at least one processor; and
   at least one memory including computer program code;
   the at least one memory and the computer program code configured to, with the at least one processor, cause the apparatus to:
   maintain at least two reference activity data items relating to previous activities, which reference activity data items comprise reference activity data associated with reference environmental data, wherein the reference activity data comprises a reference route with waypoints and the reference environmental data comprises reference wind information, captured earlier;
   process the at least two reference activity data items to provide a virtual reference activity data item using a mean value of two closest reference data items based on the environmental data, wherein the virtual reference activity data item comprises virtual reference activity data associated with virtual reference environmental data;
   determine the virtual reference activity data associated with the virtual reference environmental data corresponding to the current environmental data;
   receive current activity data and current environmental data comprising current wind information relating to a current activity;
   compare the current activity data with the virtual reference activity data; and
   provide real-time performance feedback for a user of the apparatus in response to the comparison during the current activity.

2. The apparatus of claim 1, wherein the environmental data comprises at least one of the following:
   topography information; and
   wind information.

3. The apparatus of claim 2, wherein the topography information comprises at least one of the following:
   flute height information; and
   ground slope information.

4. The apparatus of claim 1, wherein the apparatus further comprises at least one of the following devices for providing the current environmental data:
   an anemometer for providing wind information;
   a sensor for providing flute height information; and
   a satellite based positioning device for providing location information.

5. The apparatus of claim 4, wherein the location information comprises at least one of the following:
   position coordinates;
   speed;
   direction of movement; and
   slope information.

6. A method comprising:
   maintaining at least two reference activity data items relating to previous activities, which reference activity data items comprise reference activity data associated with reference environmental data, wherein the reference activity data comprises a reference route with waypoints and the reference environmental data comprises reference wind information, captured earlier;
   processing the at least two reference activity data items to provide a virtual reference activity data item using a mean value of two closest reference data items based on the environmental data, wherein the virtual reference activity data item comprises virtual reference activity data associated with virtual reference environmental data;

determining the virtual reference activity data associated with the virtual reference environmental data corresponding to the current environmental data;

receiving current activity data and current environmental data comprising current wind information relating to a current activity;

comparing the current activity data with the virtual reference activity data; and providing real-time performance feedback for a user of an apparatus in response to the comparison during the current activity.

7. The method of claim 6, wherein the environmental data comprises at least one of the following:
topography information; and
wind information.

8. The method of claim 7, wherein the topography information comprises at least one of the following:
flute height information; and
ground slope information.

9. The method of claim 6, further comprising receiving at least one of the following:
wind information;
flute height information; and
location information.

10. The method of claim 9, wherein the location information comprises at least one of the following:
position coordinates;
speed;
direction of movement; and
slope information.

11. The method of claim 6, wherein the activity data comprises at least one of the following:
sailing data; and
cycling data.

12. A computer program product embodied on a non-transitory computer readable medium comprising computer executable program code, which code, when executed by at least one processor of an apparatus, causes the apparatus to:

maintain at least two reference activity data items relating to previous activities, which reference activity data items comprise reference activity data associated with reference environmental data, wherein the reference activity data comprises a reference route with waypoints and the reference environmental data comprises reference wind information, captured earlier;

process the at least two reference activity data items to provide a virtual reference activity data item using a mean value of two closest reference data items based on the environmental data, wherein the virtual reference activity data item comprises virtual reference activity data associated with virtual reference environmental data;

determine the virtual reference activity data associated with the virtual reference environmental data corresponding to the current environmental data;

receive current activity data and current environmental data comprising current wind information relating to a current activity;

compare the current activity data with the virtual activity data; and provide real-time performance feedback for a user of the apparatus in response to the comparison during the current activity.

* * * * *